United States Patent
Svenson et al.

(10) Patent No.: US 7,812,153 B2
(45) Date of Patent: Oct. 12, 2010

(54) PROCESS FOR MANUFACTURING HIGH PURITY XYLOSE

(75) Inventors: Douglas R. Svenson, Brunswick, GA (US); Jian Li, Richmond Hill, GA (US)

(73) Assignee: Rayonier Products and Financial Services Company, Fernandina Beach, FL (US)

( * ) Notice: Subject to any disclaimer, the term of this patent is extended or adjusted under 35 U.S.C. 154(b) by 275 days.

(21) Appl. No.: 10/797,938

(22) Filed: Mar. 11, 2004

(65) Prior Publication Data

US 2005/0203291 A1    Sep. 15, 2005

(51) Int. Cl.
  *C07H 1/06* (2006.01)
  *C07H 1/00* (2006.01)
(52) U.S. Cl. ...................... 536/127; 536/124
(58) Field of Classification Search ............. 536/124, 536/127
  See application file for complete search history.

(56) References Cited

U.S. PATENT DOCUMENTS

| | | | |
|---|---|---|---|
| 3,832,276 A * | 8/1974 | Roymoulik et al. ........... 162/65 |
| 3,985,815 A | 10/1976 | Jaffe et al. |
| 3,988,198 A * | 10/1976 | Wilson et al. ............. 162/30.1 |
| 4,008,285 A | 2/1977 | Malaja et al. |
| 4,023,982 A | 5/1977 | Knauth |
| 4,066,711 A | 1/1978 | Melaja et al. |
| 4,072,538 A | 2/1978 | Fahn et al. |
| 4,075,406 A | 2/1978 | Melaja et al. |
| 4,102,705 A | 7/1978 | Pfeiffer et al. |
| 4,137,395 A | 1/1979 | Buckl et al. |
| 4,168,988 A | 9/1979 | Riehm et al. |
| 4,200,692 A | 4/1980 | Puls et al. |
| 4,246,431 A | 1/1981 | Munir et al. |
| 4,275,159 A | 6/1981 | Puls et al. |
| 4,294,654 A * | 10/1981 | Turner ........................ 162/50 |
| 4,361,463 A | 11/1982 | Lindberg et al. |
| 4,681,935 A * | 7/1987 | Forss et al. ................... 536/56 |
| 4,752,579 A | 6/1988 | Arena et al. |
| 5,081,026 A | 1/1992 | Heikkila et al. |
| 5,084,104 A | 1/1992 | Heikkila et al. |
| 5,096,820 A | 3/1992 | Leleu et al. |
| 5,125,977 A | 6/1992 | Grohmann et al. |
| 5,139,617 A | 8/1992 | Tikka et al. |
| 5,238,826 A | 8/1993 | Leleu et al. |
| 5,340,403 A | 8/1994 | Fields et al. |
| 5,589,033 A | 12/1996 | Tikka et al. |
| 5,714,602 A | 2/1998 | Beck et al. |
| 5,932,452 A | 8/1999 | Mustranta et al. |
| 5,951,777 A | 9/1999 | Nurmi et al. |
| 5,998,607 A | 12/1999 | Heikkila et al. |
| 6,057,438 A | 5/2000 | Hyatt et al. |
| 6,086,681 A | 7/2000 | Lindroos et al. |
| 6,110,323 A | 8/2000 | Marsland |
| 6,239,274 B1 | 5/2001 | Heikkila et al. |
| 6,262,318 B1 | 7/2001 | Heikkila et al. |
| 6,291,725 B1 | 9/2001 | Chopade et al. |
| 6,303,353 B1 | 10/2001 | Sugiyama et al. |
| 6,340,582 B1 | 1/2002 | Suzuki et al. |
| 6,451,123 B1 | 9/2002 | Saska et al. |
| 6,458,570 B1 | 10/2002 | Elseviers et al. |
| 6,485,667 B1 * | 11/2002 | Tan ........................... 264/510 |
| 6,512,110 B1 | 1/2003 | Heikkila et al. |
| 6,538,133 B1 | 3/2003 | Aoki et al. |
| 6,548,662 B1 | 4/2003 | Ohsaki et al. |
| 2004/0020854 A1 | 2/2004 | Ali et al. |

FOREIGN PATENT DOCUMENTS

WO    WO 9714803 A1 *   4/1997
WO    WO 00/61276       10/2000

OTHER PUBLICATIONS

Smook, *Second Edition Handbook for Pulp & Paper Technologists*, "Chemistry of Kraft Pulping—Prehydrolysis Stage for Dissolving Grades (p. 79)," pp. 77-79, 1992.

* cited by examiner

*Primary Examiner*—Shaojia Anna Jiang
*Assistant Examiner*—Everett White
(74) *Attorney, Agent, or Firm*—Alston & Bird LLP

(57) ABSTRACT

A process for manufacturing xylose by extracting hemicellulose from a cellulosic material, such as by a cold caustic extraction method, concentrating the extract, such as by nanofiltration, into a hemicaustic stream containing hemicellulose with greater than about 85 wt % xylan content, and subsequently hydrolysing the xylan from the hemicaustic stream to xylose. The high concentration of xylan within the concentrated hemicaustic stream enables hydrolyzation of the xylan to food-grade xylose and, optionally, hydrogenation of the xylose to xylitol without the need of a chromatographic separation step as previously required.

39 Claims, 8 Drawing Sheets

PROCESS FOR MANUFACTURING HIGH PURITY XYLOSE

FIELD OF THE INVENTION

This invention relates to the treatment of cellulosic fibers. More particularly, the invention relates to extraction of hemicellulose from cellulose pulp and conversion of xylan within the extracted hemicellulose to xylose.

BACKGROUND OF THE INVENTION

Xylose is a 5-carbon sugar of wide-scale commercial interest, primarily because it may be easily hydrogenated to xylitol, which is used as a specialty sweetener in the food, drug, and confectionary industries. Xylan, a natural occurring polymer of xylose, commonly referred to as a pentosan, and one of the five principal components of hemicellulose, can be converted to xylose by hydrolysis. Therefore, extraction of xylan from cellulosic fibers is of interest.

The dry weight components of arboreal wood, such as hardwood pulps from sources including sweet gum, black gum, maple, oak, eucalyptus, poplar, beech, aspen, and mixtures thereof, are roughly 30% hemicellulose, 42% cellulose, 25% lignin, and 3% wood extractives. The exact quantity of each component varies between species, and within a given species depending on the age of a tree, where it grows, etc.

Hemicelluloses are linear polymers composed of cyclic 5-carbon and 6-carbon sugars (polysaccharides). There are five main classes of hemicellulose, namely galactoglucomannan, arabinoglucuronoxylan, arabinogalactan, glucuronoxylan, and glucomannan. In hardwood species, 75-95% of the hemicellulose is of the glucuronoxylan type. In its native state, hardwood hemicellulose has an average degree of polymerization (DP) of approximately 200, and 80-90% of the principal monomer components are anhydrous D-xylose units.

Cellulose is the main component of wood, contributing 40-45% to the total dry mass. Cellulose is located almost entirely in the cell wall of wood fibers. Like hemicellulose, cellulose is a linear polymer. However, the DP of cellulose is much higher, typically between 1,000 to 10,000, and cellulose chains are composed entirely of anhydrous D-glucose units.

Lignin is a network polymer composed of phenyl-propane monomers, namely ρ-coumaryl alcohol, coniferyl alcohol, and sinapyl alcohol, which are generally referred to as cinnamyl alcohols, and are commonly called lignin C9-units. It contributes to approximately 15% to 35% of the dry mass of softwoods, hardwoods, and woody grasses. Lignin is deposited between individual wood fibers and acts as an intercellular adhesive, binding individual wood fibers together.

"Pulping" is the process of chemically or mechanically liberating the individual cellulosic fibers in wood. In North America, the kraft cooking process is the predominant pulping process although there are other pulping practices, such as sulfite pulping, soda/AQ pulping, solvent pulping, mechanical pulping, and the like, which are all well known in the art. The kraft process is a chemical pulping process where chipped wood is "cooked" or digested in a high temperature broth of sodium hydroxide and sodium sulfide cooking liquor. During cooking, lignin and hemicellulose macromolecules are fragmented and solvated, thereby breaking the intercellular adhesive between wood fibers and allowing separation of a pulp extract stream from the cellulose pulp.

Conventional methods of obtaining xylan involve the pulping of wood to separate the lignin and hemicellulose from the cellulose of the wood fibers, and, thereafter, separating xylan from other pulp extracts. However, the traditional steps required to separate xylan from wood lignin, and other non-xylose containing pulp extracts, requires costly and complex purification steps. Prior art purifies xylan using a precipitation step, and/or the xylose produced by hydrolyzing xylan is purified by chromatographic separation. For instance, Hyatt et al., U.S. Pat. No. 6,057,438, discloses a method of combining the effluent from multiple stages of a hardwood cooking process and recovering xylan therefrom. However, recovery of xylan requires an alcohol precipitation step due to the amount of non-xylan organics in the effluent that must be separated from the xylan. Meleja, et al., U.S. Pat. No. 4,075,406, discloses a method of recovering xylose from pentosan containing raw materials by hydrolyzing the raw materials and then purifying the hydrolyzate. However, the hydrolyzate must afterward be subjected to chromatographic fractionation in order to separate xylose from the solution. Heikkila, et al., U.S. Pat. No. 5,084,104 similarly discloses a method of hydrolyzing a pentosan containing raw material and then purifying the hydrolyzate. Likewise, Heikkila requires that the hydrolyzed material be chromatographically separated to obtain pure xylan. As mentioned, xylose separation stages such as alcohol precipitation and chromatographic separation are costly and undesirable.

It is desired to provide a method of utilizing the xylan content of hemicellulose in a caustic extraction solution to make commercial grade xylose without the necessity of the costly and cumbersome pentose separation steps required in the past, namely alcohol precipitation, chromatographic separation, and the like. It is further desired to integrate the method of utilizing xylan, for the production of xylose, with current pulp processing techniques that simultaneously produce paper-grade or chemical-grade cellulosic fibers.

BRIEF SUMMARY OF THE INVENTION

The invention is a process of extracting hemicellulose from a cellulosic material that results in a concentrated hemicaustic stream containing hemicellulose with greater than about 85 wt % xylan content and subsequently hydrolyzing the xylan to xylose. The invented process optionally includes the step of hydrogenating the xylose to xylitol without the need of a chromatographic separation step as previously required.

According to one embodiment, the process comprises the steps of sequentially: subjecting an at least partially bleached hardwood pulp to an alkaline treatment to extract hemicellulose from the pulp into a hemicaustic solution, and separating the hemicaustic solution into a purified caustic stream and concentrated hemicellulose solution, such as by nanofiltration, and hydrolyzing the xylan content of the concentrated hemicellulose solution to xylose. For example, the concentrated hemicaustic solution may be neutralized by the addition of a mineral acid, and the xylan-rich hemicellulose may then be acid hydrolyzed to xylose.

Following the above process steps in accordance with this specification results in a concentrated hemicellulose solution of about 5 wt % to about 30 wt % hemicellulose, and less than about 1 wt % of lignin and other impurities. Because the hemicellulose results from the processing of a high xylan content pulp, between 85% and 99% of the hemicellulose is xylan. As a result, the subsequent hydrolysis of the xylan within the concentrated hemicellulose solution results in a xylose product with a purity greater than about 80 wt % without the need of additional purification steps such as chromatography and precipitation.

According to another embodiment, xylose produced in accordance with this specification may be hydrogenated to xylitol.

The production of xylose and, optionally, xylitol occurs without the need for the chromatographic or similar separating steps required in past methods of xylose and xylitol production. Methods of the past have required the removal of relatively large excesses of lignin from xylose mixtures, or the removal of relatively large excesses of non-xylose containing components from hemicellulose prior to, or after, conversion to xylose. These past separations have required costly chromatographic separation or alcohol precipitation steps. The concentrated hemicaustic stream resulting from the disclosed process has such a low lignin concentration and such a high concentration of xylose, that chromatography and precipitation may be avoided completely. Thus, cost, time, and processing inefficiencies associated with the chromatographic and precipitation separation steps are avoided.

BRIEF DESCRIPTION OF THE SEVERAL VIEWS OF THE DRAWINGS

Figure 2:
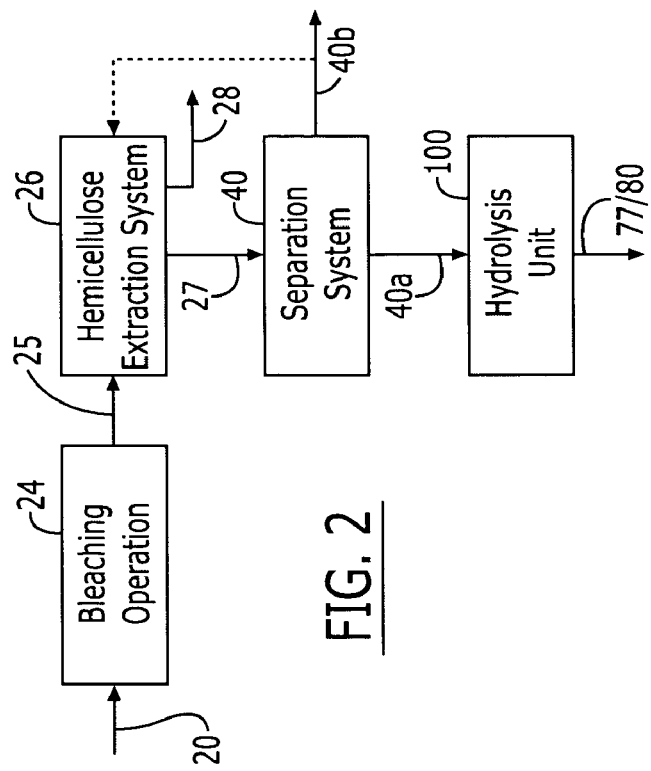
Figure 1:
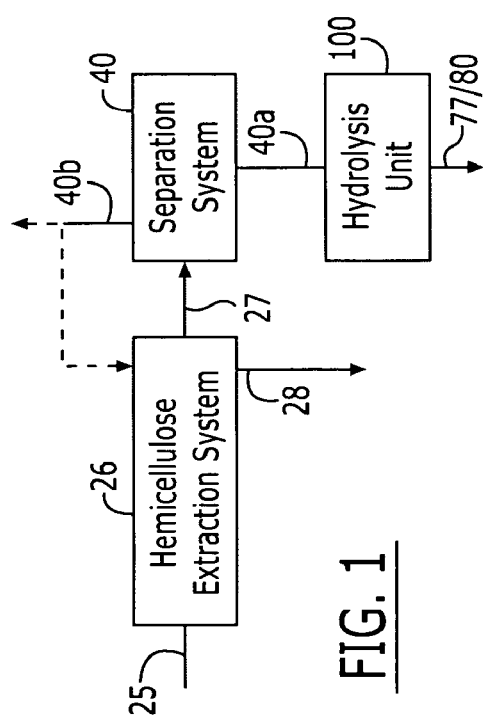
Figure 3:
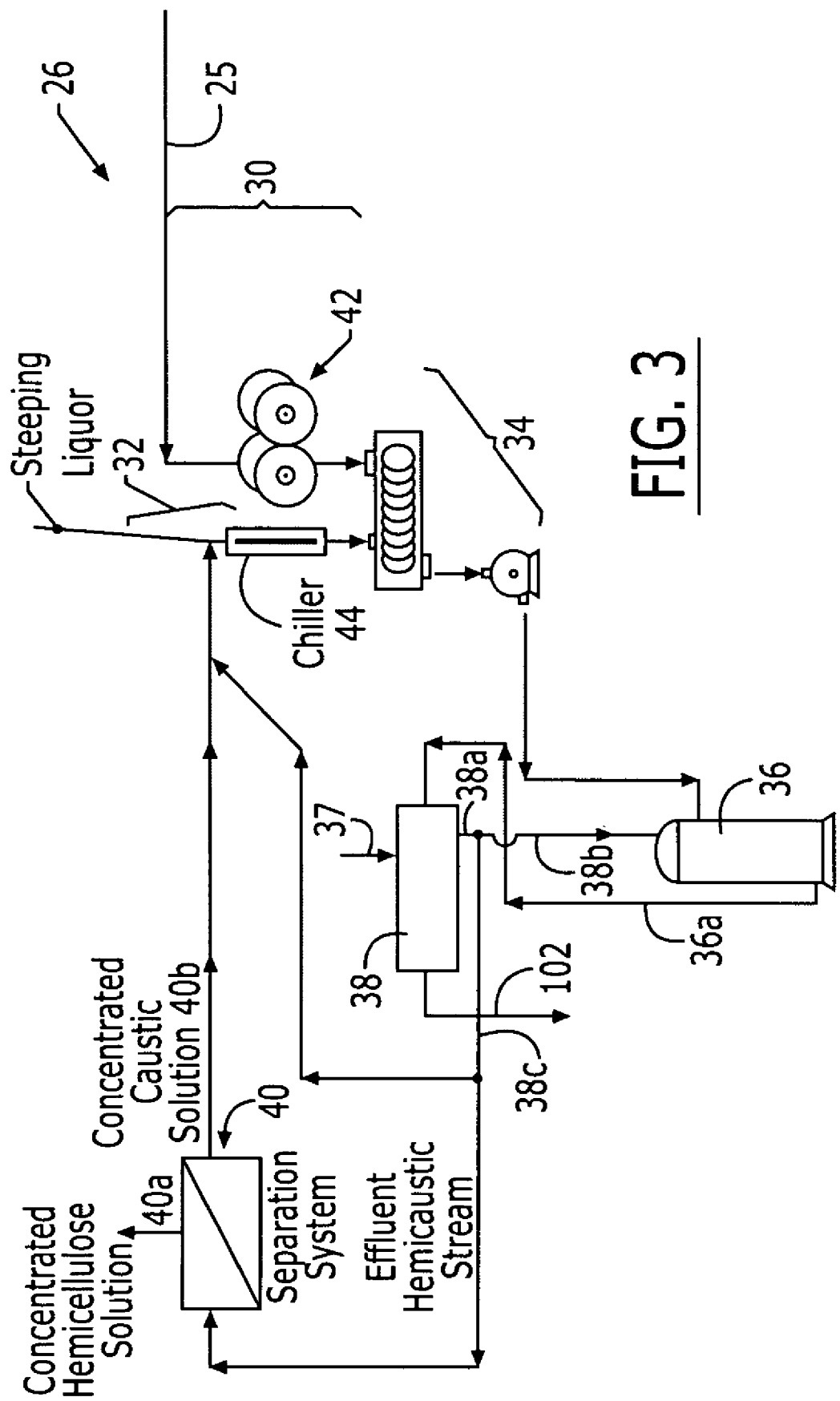
Figure 4:
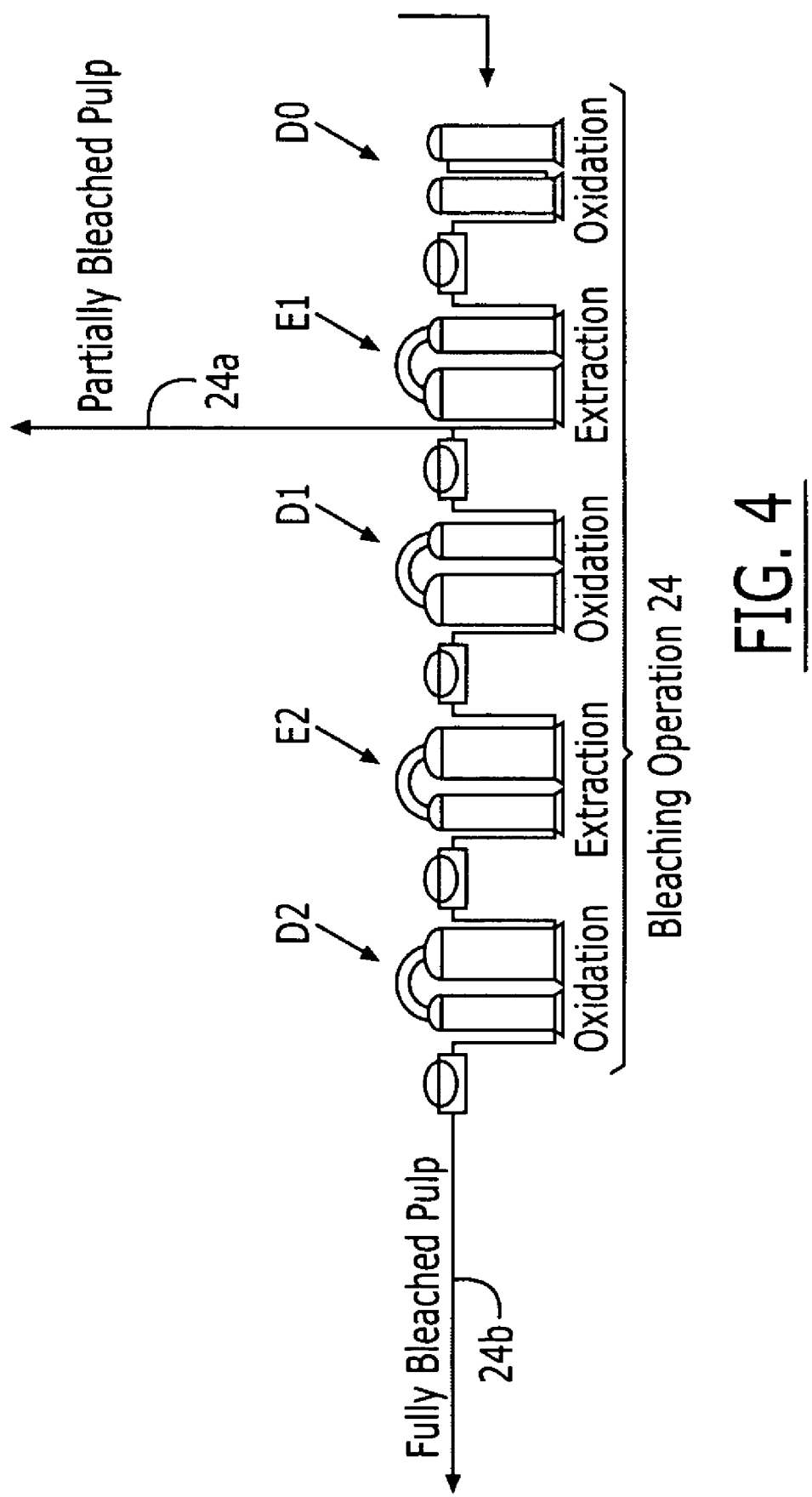
Figure 5:
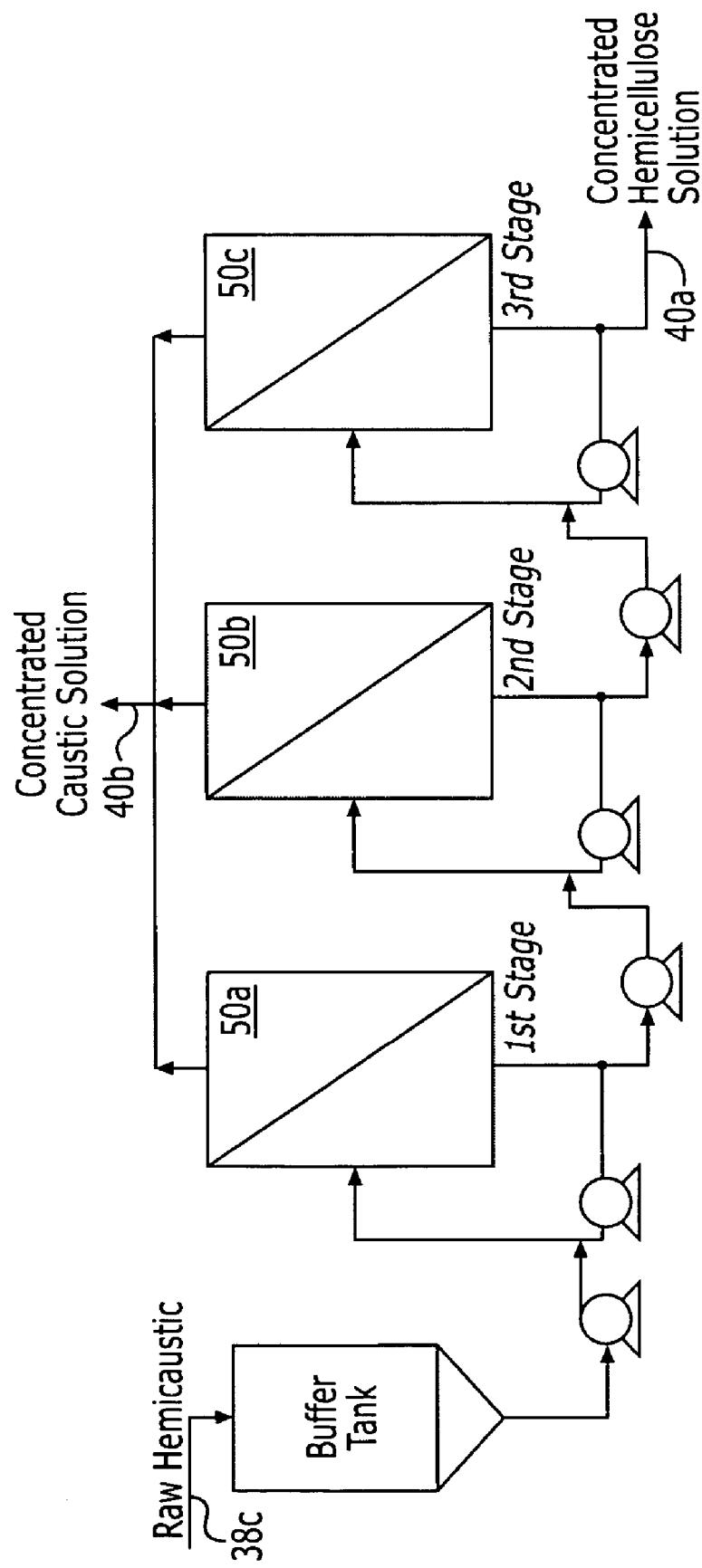
Figure 6:
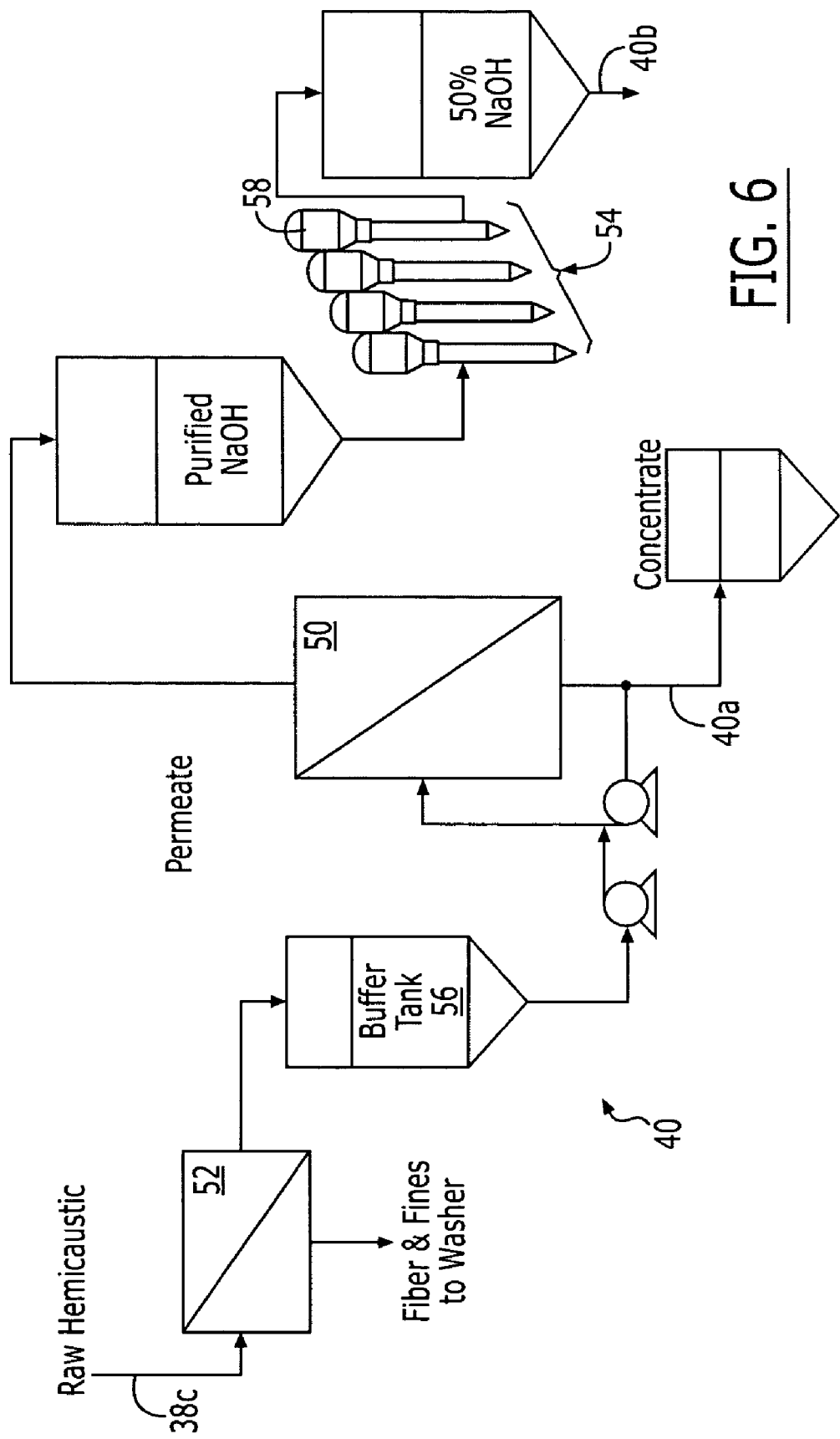
Figure 7:
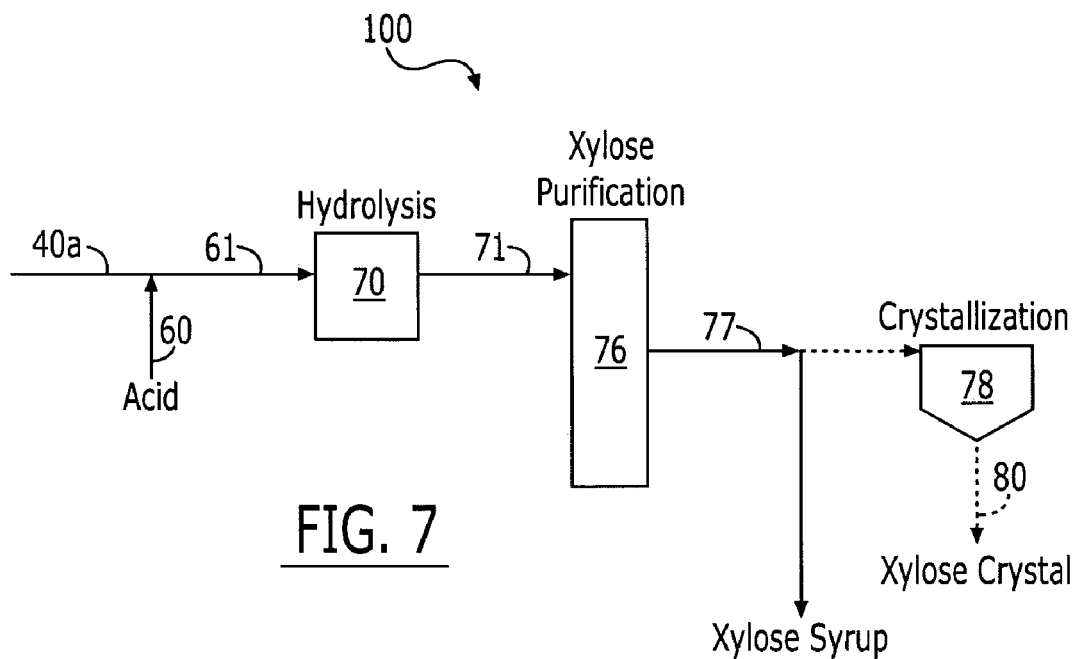
Figure 8:
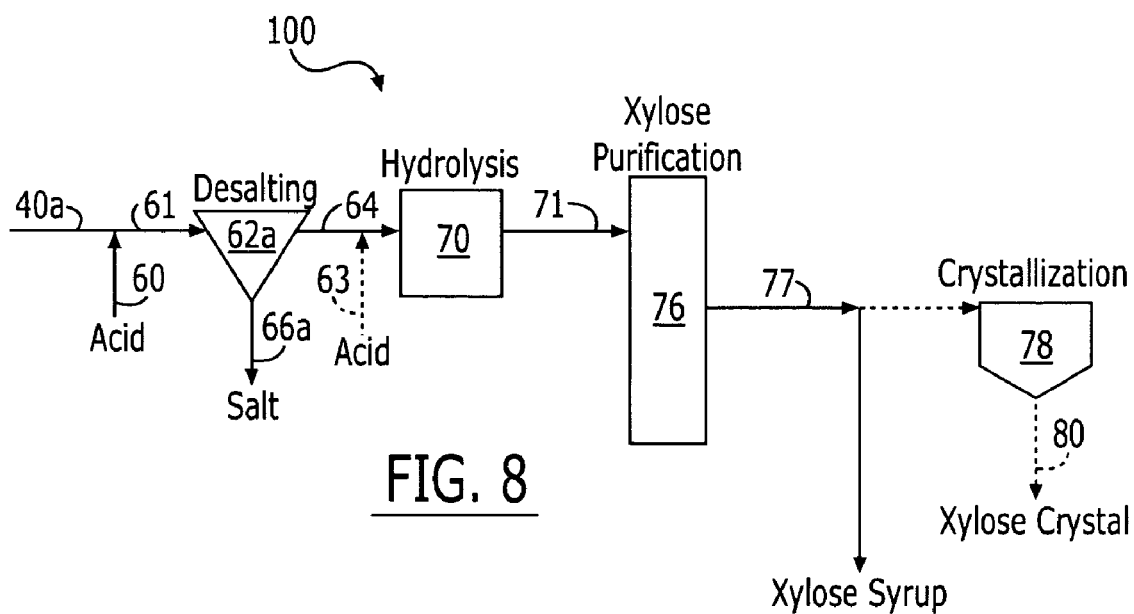
Figure 9:
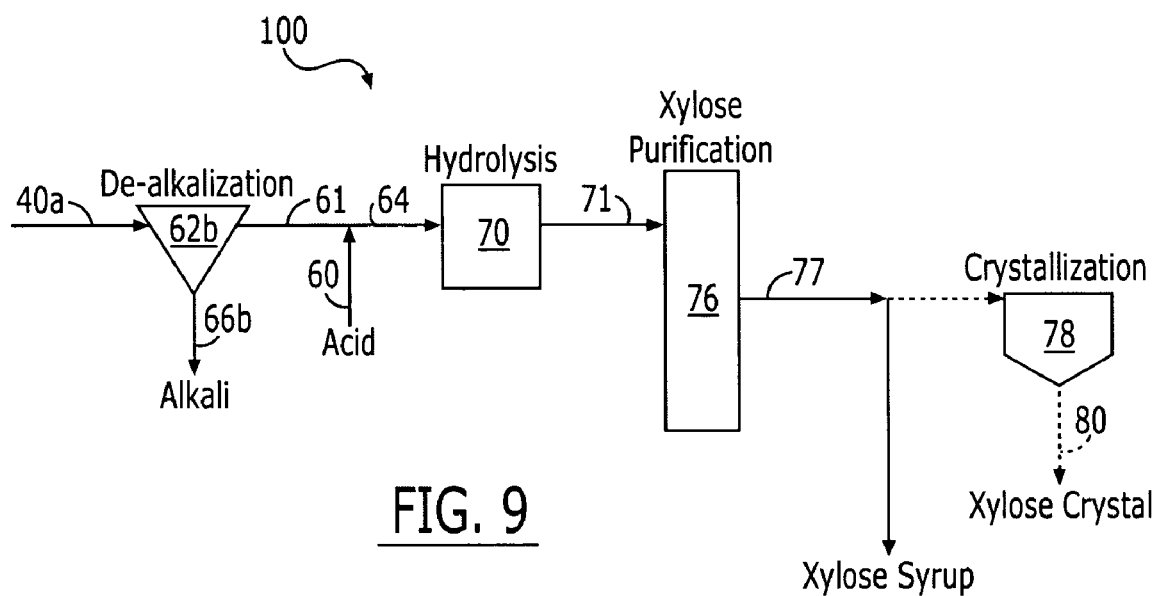
Figure 10:
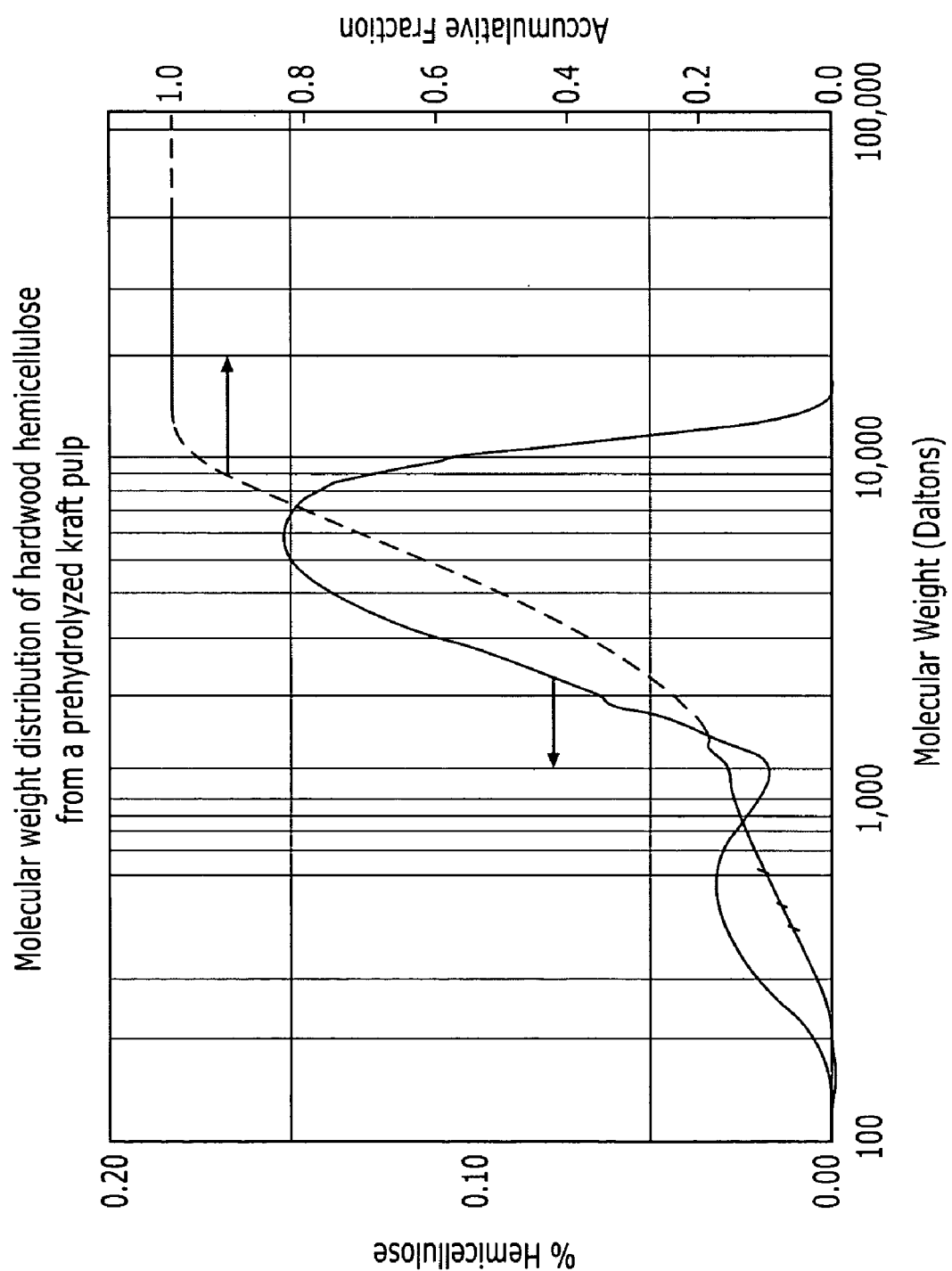

Having thus described the invention in general terms, reference will now be made to the accompanying drawings, which are not necessarily drawn to scale, and wherein:

FIG. 1 is a flow diagram showing the process of the invention according to one embodiment;

FIG. 2 is a flow diagram showing the process of the invention according to another embodiment;

FIG. 3 is a flow diagram of an alkaline treatment system in accordance with an embodiment of the invention;

FIG. 4 is a flow diagram of a bleaching operation used in accordance with an embodiment of the invention;

FIG. 5 is a flow diagram of a nanofiltration separation system in accordance with an embodiment of the invention;

FIG. 6 is a flow diagram of a nanofiltration separation system in accordance with another embodiment of the invention;

FIG. 7 is a flow diagram of a hydrolysis operation in accordance with an embodiment of the invention;

FIG. 8 is a flow diagram of a desalting and hydrolysis operation in accordance with an embodiment of the invention;

FIG. 9 is a flow diagram of a de-alkalization and hydrolysis operation in accordance with an embodiment of the invention; and, FIG. 10 is a chromatograph showing the molecular weight of hemicellulose of an exemplary hemicellulose extract from a pre-hydrolyzed kraft hardwood pulp.

DETAILED DESCRIPTION OF THE INVENTION

Hereinafter, the present inventions will now be described more fully with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Referring to FIG. 1, in general, the invented method comprises providing an at least partially bleached pulp 25 from a cellulose-based material that contains hemicellulose, wherein the hemicellulose content of the pulp is predominantly xylan. The pulp is transferred to a hemicellulose extraction system 26 where the hemicellulose is extracted from the pulp into a caustic solution. After extraction, the hemicaustic solution 27 (aqueous caustic and dissolved hemicellulose) is washed from the pulp 28. The hemicaustic solution 27 is separated in a separation system 40 into a concentrated hemicellulose solution 40a and a purified caustic solution 40b. The purified caustic solution 40b is optionally fed back to the hemicellulose extraction system 26. The hemicellulose from the concentrated hemicellulose solution 40a is hydrolyzed in a hydrolysis unit 100. The hydrolysis converts the xylan within the hemicellulose to xylose 77/80.

The feed stream 25 to the hemicellulose extraction system 26 is an aqueous stream of at least partially bleached cellulose pulp having a relatively low lignin content, below about 1 wt %, and a hemicellulose content above about 4 wt % and of which the hemicellulose is greater than about 85 wt % xylan. The partially bleached pulp may be obtained from an external source or may be the output stream of a bleaching operation.

According to an advantageous embodiment shown in FIG. 2, the feed stream 25 is advantageously the result of a pulp 20 that is at least partially chemically bleached in a bleaching operation 24. After being at least partially bleached, the pulp is transferred to the hemicellulose extraction system 26 where most of the hemicellulose content of the bleached pulp is extracted into a caustic liquor 27. The hemicellulose extraction system 26 is advantageously placed after the bleaching operation 24 because most lignin will have been removed from the pulp at this point, resulting in a relatively lignin-free extract. The hemicellulose extraction system 26 may be placed in front of the bleach operation 24. However, such placement is generally unfavorable because the extract would have a high contamination of lignin, most likely resulting in the need for additional purification steps in the xylose manufacturing process.

Because the hemicellulose extraction system 26 is downstream of the partial or complete bleaching operation 24, the cellulosic slurry provided to the hemicellulose extraction system 26 would, thus, typically be expected to have a fairly low lignin content, i.e. a reduction of about 80 wt % or greater than the original lignin content of the unbleached fiber (brown stock). The fibers within the cellulosic slurry provided to the hemicellulose extraction system 26 contains up to 30 wt % hemicellulose (oven dried basis).

The at least partially bleached pulp 25 is typically supplied to the hemicellulose extraction system 26 as an aqueous slurry and combined with an alkaline, or caustic, solution commonly referred to as the steeping liquor. Conventional wisdom has generally taught that in order to ensure proper mixing of the cellulosic fibers and the alkaline solution during caustic treatments, the incoming cellulose slurry should have a fairly low consistency. Consequently, cellulosic pulps subjected to a hemicellulose extraction 26 have heretofore generally been characterized by a relatively low consistency, such as a consistency of about 3 wt %. However, such dilute cellulosic fiber slurries result in the use of more alkaline solution than ideally required, thus increasing production costs.

Applicants have determined that cellulosic fiber slurries having an intermediate consistency may beneficially be subjected to caustic treatments. More particularly, Applicants have determined that the use of intermediate cellulose slurry consistencies during hemicellulose extraction provides an acceptable balance between lower consumption of alkaline solution and proper mixing of steeping liquor and cellulosic fiber.

Exemplary cellulose slurry consistencies suitable for use in the hemicellulose extraction stage of the present invention include consistencies ranging from about 10 to 50 wt %. In one advantageous embodiment, a consistency of about 20 wt % is employed. As used herein, the term "consistency" refers to the concentration of the cellulosic fibers present in the cellulose slurry. Consequently, the consistency will be presented as a weight percent representing the weight amount of the cellulosic fibers present in the cellulose slurry divided by the total weight amount of cellulosic slurry, multiplied by 100.

As illustrated in FIG. 3, an exemplary hemicellulose extraction system 26 is a cold caustic treatment system. The exemplary cold caustic treatment system is described in greater detail in Ali et al., U.S. Patent Application Publication 2004/0020854. The cold caustic treatment generally includes a cellulose slurry supply system 30; a steeping liquor supply system 32; a mixing system 34 to combine the cellulose slurry and steeping liquor; at least one alkaline treatment unit 36; at least one treated cellulose washer 38 to remove the hemicaustic from the treated cellulose slurry; and a separation system 40 to treat the effluent hemicaustic stream. The hemicellulose extraction system 26 of the present invention typically treats wood pulp streams in the form of cellulosic slurries at flow rates and concentrations typical of those known in the art.

The incoming cellulose slurry of partially bleached pulp 25 entering the hemicellulose extraction system 26 from the bleaching operation 24 typically has a fairly low consistency, such as a consistency up to 15 wt %, to ease bulk transport properties and the like. A significant quantity of steeping liquor is added to the already dilute cellulose slurry during the alkaline treatment process, further decreasing the consistency. Consequently, to ensure a suitable consistency following the addition of the steeping liquor, the cellulose slurry supply system 30 may advantageously include a slurry concentrator 42 to increase the consistency of the incoming cellulose slurry. The slurry concentrator 42 beneficially includes at least one press. Exemplary presses for use as the slurry concentrator include twin roll presses and screw presses. In advantageous embodiments, at least one twin roll press is utilized as the slurry concentrator. Any twin roll press capable of processing cellulose slurries in accordance with the present invention may be employed. One exemplary twin roll press is commercially available from Metso.

The slurry concentrator 42 may increase the consistency of the incoming cellulose slurry up to 50%. For example, the slurry concentrator may provide a comparatively high consistency cellulose slurry to the mixer 34 which ranges in consistency from about 10 to 50 wt %, such as a comparatively high consistency cellulose slurry having a consistency of about 20 wt %.

The steeping liquor supply system 32 provides a steeping liquor containing an alkaline solution to the mixer. The alkaline solution generally includes a caustic compound, i.e. a compound capable of providing a pH of above 7, dispersed in water. The caustic compound is typically formed from at least one alkali metal salt. Suitable alkali metal salts include, but are not limited to, sodium hydroxide, potassium hydroxide and mixtures thereof. In an alternative embodiment, ammonium hydroxide may be employed as the caustic compound. The concentration of caustic in the steeping liquor introduced into the mixing system 34 typically ranges from about 3 to about 50 wt %. In one beneficial embodiment, the concentration of the caustic compound in the steeping liquor introduced into the mixing system 34 is about 25 wt %. Sufficient steeping liquor is supplied to the mixing system 34 to produce an alkaline cellulose slurry within the mixing system 34 containing 2 to 20 wt % caustic compound, such as an alkaline cellulose slurry within the mixing system 34 containing about 26 wt % caustic compound. The alkaline cellulose slurry within the mixing system 34 typically exhibits a pH above 13.

The steeping liquor supply system 32 optionally comprises at least one chiller 44. The incoming steeping liquor is typically supplied to the hemicellulose extraction treatment system 26 at temperatures ranging from about 20 to 90° C. However, the chiller 44 advantageously reduces the temperature of the steeping liquor supplied to the mixing system 34 to the range from about 15° C. to about 40° C.

The high consistency cellulose slurry exiting the slurry concentrator 42 is blended with the steeping liquor in a mixing system 34 to form an alkaline cellulose slurry. The mixing system 34 generally includes at least one in-line mixer. The in-line mixer may be any mixer known in the art capable of mixing alkaline cellulose slurries at consistencies of the present invention. Exemplary in-line mixers include, but are not limited to, screw conveyors, rotor/stator mixers and hydraulic piston mixers. The mixing system typically includes two mixers, beneficially arranged in series.

The alkaline cellulose slurry exiting the mixing system 34 is transported to at least one hemicellulose extraction unit 36 for steeping the alkaline cellulose slurry provided by the mixing system 34 for a sufficient amount of time to diffuse an effective amount of the hemicellulose out of the cellulosic fibers and into the steeping liquor. The hemicellulose extraction unit 36 is generally a large jacketed vessel providing suitable agitation and dwell time to allow the alkaline cellulosic slurry to effectively steep. Any suitable reactor or vessel may be employed as the hemicellulose extraction unit 36.

The hemicellulose extraction, specifically the steeping within the hemicellulose extraction unit 26, is typically conducted at comparatively low temperatures, as known in the art. For example, these "cold caustic treatments" are generally carried out at temperatures less than about 50° C., and advantageously at a temperature less than 40° C., such as a temperature between about 20° C. and about 40° C. In one beneficial embodiment, the cold caustic treatment may be conducted at a temperature of about 30° C.

The alkaline cellulose slurry is allowed to steep or react within the hemicellulose extraction unit 36 for a sufficient amount of time to diffuse an effective amount of the hemicellulose out of the cellulosic fibers and into the steeping liquor. The alkaline cellulose slurry may steep or react within the extraction unit 36 for exemplary dwell times up to 4 hours.

The treated cellulose fibers within the treated cellulosic slurry exiting the hemicellulose extraction unit 36 generally contain no more than 15 wt % hemicellulose, and typically no more than 6 wt % hemicellulose if the raw wood source was pre-hydrolyzed. The steeping liquor exiting the hemicellulose extraction unit 36 generally contains from about 0.5 to 7 wt % hemicellulose.

The treated cellulose slurry 36a is transported from the hemicellulose extraction unit 36 to at least one washer 38 to separate the spent steeping liquor and dissolved hemicellulose from the treated cellulosic fibers. The washer 38 may be any suitable wet process by which to extract the spent steeping liquor and hemicellulose from the treated cellulose slurry. Exemplary washers 38 for use in the present invention include, but are not limited to, horizontal belt washers, rotary drum washers, vacuum filters, wash presses, compaction baffle (CB) filters, atmospheric diffusers and pressure diffusers. In one advantageous embodiment, the washer 38 is a horizontal belt washer. Horizontal belt washers generally employ a series of showers emitting either fresh or recycled wash water onto the treated cellulose slurry as it travels through the machine on a continuous screen or mesh belt, as known in the art. Similar to the brown stock washers described earlier, horizontal belt washers subject the treated cellulosic slurry to progressively cleaner water, with the wash water moving counter currently against the progression of the pulp from shower to shower so that the cleanest pulp is washed with the cleanest water in the last shower and the dirtiest pulp is washed with the dirtiest water in the first shower. Horizontal belt washers are commercially available as CHEMIWASHER™ from Kadant Black Clawson.

The wash water 37 entering the washer 38 is advantageously purified water, such as water that has been transported through a zeolite bed or the like. The wash water may further contain conventional additives known in the art of pulp washing, such as surface tension modifiers and the like. A sufficient amount of wash water is applied to the treated cellulose slurry traveling through the washer 38 to remove up to 100% of the dissolved hemicellulose and up to 100% of the steeping liquor containing the caustic compound from the incoming treated cellulose slurry.

The spent wash water stream 38a exiting the treated cellulose washer 38, commonly referred to as the hemicaustic stream, generally includes hemicellulose, unreacted caustic compound from the steeping liquor, and water. The hemicaustic stream exiting the washer 38 typically includes from about 0.5 to 7 wt % of hemicellulose. The hemicaustic stream exiting the washer 38 further generally includes up to 20 wt % of caustic compound, with the remainder being water and any optional additives that may have been included in either the steeping liquor or wash water. The hemicaustic stream typically exhibits a pH above 13.

The treated cellulose slurry supplied to the washer 38 advantageously exhibits a comparatively low consistency, such as a consistency ranging from about 2 to 4 wt %. However, the treated cellulose slurry exiting the alkaline treatment unit 36 typically exhibits a consistency ranging from about 2 to 12 wt %, i.e. the consistency of the treated cellulosic slurry is comparable to the consistency of the alkaline cellulose slurry exiting the mixing system 34. Therefore, to provide treated cellulose slurry having a suitable consistency to the washer 38, a portion 38b of the hemicaustic stream exiting the washer 38 may be diverted and used to lower the consistency of the treated cellulose slurry stream entering the washer. For example, up to 80% of the hemicaustic stream exiting the washer 38 may be diverted and mixed with the treated cellulose slurry exiting the alkaline treatment unit.

The washed pulp 102 leaving the washer 38 is a paper-grade or chemical-grade pulp that may be used in further processes. The chemical-grade pulp may be used to produce cellulose esters and other cellulose derivatives. Chemical-grade pulp typically contains less than about 5 wt % hemicellulose with only traces of lignin, and is advantageously prepared from fully bleached, pre-hydrolyzed pulp. The paper-grade pulp typically contains less than about 20 wt % hemicellulose with trace amounts of lignin, and may be prepared from partially bleached pulp that may or may not be pre-hydrolyzed.

The hemicellulose extraction system 26 is described herein as a cold caustic treatment system because cold caustic treatment is particularly effective at removing high quantities of hemicellulose from a cellulose pulp. The cold caustic treatment stands in contrast to conventional lignin extraction processes, which typically use low concentrations of caustic (usually about 0.1 wt % to about 0.5 wt % NaOH in solution), high temperatures (typically about 180° F.), and in general do not dissolve any appreciable quantities of hemicellulose. It should be understood that the systems and methods of the present invention may be used in conjunction with alkaline treatments, other than cold caustic treatments, to purify the hemicellulose and cellulose contained in pulps prior to hemicellulose extraction.

At least a portion 38c of the remaining, i.e. undiverted, hemicaustic stream is transported from the treated cellulose washer 38 to a dissolved solids separation system 40 capable of separating the portion 38c of the hemicaustic stream into a purified caustic solution stream 40a and a concentrated hemicellulose solution 40b.

Rather than being positioned downstream of an independent bleaching operation, the hemicellulose extraction system 26 may be advantageously incorporated into one of the intermediate or later stages of the bleaching operation. Referring to FIG. 4, in one beneficial embodiment, the hemicellulose extraction unit 36 is a reactor, such as an extraction tower, such as typically employed within wood pulp bleaching processes. If a partially bleached pulp 24a is used to feed the hemicellulose extraction system 26, and if the third, fourth, and fifth stages ($D_1$, $E_2$, and $D_2$) are not otherwise utilized in the bleaching operation, the remaining extraction tower $E_2$ of the bleaching operation 24 may advantageously be used as the hemicellulose extraction unit 36. If a fully bleached pulp 24b is used to feed the hemicellulose extraction system 26, or if the extraction tower $E_2$ is otherwise unavailable, then the hemicellulose extraction system 26 could use a separate vessel.

According to another advantageous embodiment, the raw cellulose feedstock used with the invented method may be pre-hydrolyzed prior to pulping. Methods of prehydrolyzation are known in the art of paper making. Pre-hydrolyzation is advantageous because pre-hydrolysis partially decomposes and lowers the molecular weight of the hemicellulose within the wood chips that eventually result in the alkaline cellulose slurry within the alkaline treatment unit 36. Pre-hydrolyzed hemicellulose is more readily removed from cellulose fibers than hemicellulose that has not been pre-hydrolyzed. Therefore, pre-hydrolysis results in accelerated hemicellulose extraction in the hemicellulose extraction system 26, and increases the amount of hemicellulose extracted in the cold caustic treatment to near 100%.

Various methods of separating suspended and dissolved solids from a liquid medium may be used to separate the hemicaustic stream 38c. Such methods include, but are not limited to, precipitation, centrifugation, filtration, and dialysis.

According to an advantageous embodiment, the separation system 40 is a nanofiltration system. As used herein, the term "nanofiltration system" refers to a process that uses microporous membranes having a pore size smaller than those typically used in ultrafiltration processes. FIG. 5 illustrates a nanofiltration system 40 in accordance with advantageous aspects of the invention. The nanofiltration system 40 generally includes at least one nanofiltration unit and beneficially includes a plurality of nanofiltration units. In the beneficial embodiment illustrated in FIG. 5, the nanofiltration system 40 includes three nanofiltration units, 50a-50c. Each nanofiltration unit 50a-50c may advantageously include one or more nanofiltration membranes.

By use of nanofiltration membranes having the appropriate nominal molecular weight cut off or pore size, the caustic and aqueous components in the hemicaustic stream, i.e. those having a molecular size smaller than the molecular weight cut off or nominal pore diameter of the nanofiltration membrane, pass through the nanofiltration membrane and exit the nanofiltration system 40 as a permeate stream 40b. The hemicellulose components as well as residual lignin and impurities within the hemicaustic stream having a molecular size larger than the nominal molecular weight cut off of the membrane, are "rejected" by the nanofiltration membrane and exit the nanofiltration system 40 as a concentrate hemicellulose stream 40a. As indicated in FIG. 10, the majority of the hemicellulose extracted from a prehydrolyzed hardwood kraft pulp has a molecular weight greater than 200 Daltons. Therefore, in one advantageous embodiment, the nanofiltration membrane has a nominal molecular weight cut off of about 200 Daltons, thereby capturing and concentrating a large majority of the dissolved hemicellulose.

The nanofiltration membranes may be formed from a number of different polymers, as known in the art. More particularly, any polymer capable of withstanding the elevated pH's associated with the hemicaustic stream may be employed. Advantageously, the polymer used to form the nanofiltration membrane is capable of withstanding pHs above 14 for an extended period of time. Exemplary materials for use in forming ultrafiltration membranes include many commercially available polymers such as polyether-sulfone, polysulfone, polyarylether sulfones, polyvinylidene fluoride, polyvinyl chloride, polyketones, polyether ketones, polytetrafluoroethylene, polypropylene, polyamides and mixtures thereof. The degradation properties of the foregoing polymers may further be improved by altering their molecular weight distribution, as described in U.S. Pat. No. 5,279,739.

The nanofiltration system 40 may be operated at any temperature known in the art, such as at temperatures of up to about 70° C. In one advantageous embodiment, the nanofiltration system is operated at a temperature of about 50° C. The pressure at which nanofiltration is carried out is advantageously high enough to provide adequate flow through the nanofiltration membrane to achieve desired processing efficiencies. Typically, the nanofiltration system 40 may be operated at a hydrostatic pressure of from about 100 to about 500 psi, advantageously from about 300 to about 450 psi.

The nanofiltration membrane can be in a number of different configurations and are usually positioned within a cartridge type assembly or module within a larger nanofiltration unit. Preferred membrane configurations for use in the process of the present invention are commonly referred to as "spiral wound membranes." Spiral wound membranes typically include a centrally positioned permeate or filtrate tube and at least one sheet of a membrane with appropriate spacer and backing that is spirally wound around the permeate or filtrate tube.

Other suitable configurations include nanofiltration units 50 containing tubular arrays of hollow fiber membranes where a plurality of hollow membrane fibers (e.g., 3 to 20) are disposed within a modular housing. Flat sheet filter cartridges containing a series of 2 or more spaced apart nanofiltration membrane plates or sheets can also be used as a nanofiltration unit accordance with the present invention.

The nanofiltration system 40 can advantageously include a plurality of nanofiltration units arranged in series. For example, the nanofiltration system 40 may include three nanofiltration units 50a-50c arranged in series. In such advantageous embodiments, the additional nanofiltration units 50b-50c may be arranged so as to filter the concentrate exiting the previous nanofiltration unit 50a or 50b, thereby increasing the overall efficiency of the nanofiltration system relative to a nanofiltration system having a single nanofiltration unit. For example, a 400 gpm hemicaustic stream may be transported through an initial nanofiltration unit, yielding a 180 gpm permeate stream and a 220 gpm concentrate stream. A second nanofiltration unit can then be used to filter the concentrate stream exiting the first nanofiltration unit, thereby producing a 100 gpm permeate stream and 120 gpm concentrate stream. A third nanofiltration unit can then be used to filter the concentrate stream exiting the second nanofiltration unit, thereby producing a 40 gpm permeate stream and an 80 gpm concentrate stream.

FIG. 6 illustrates a further advantageous embodiment of the invention, in which the nanofiltration system 40 includes both a pre-filtration unit 52 to remove larger contaminants from the hemicaustic stream prior to nanofiltration and an evaporation system 54 to increase the concentration of the permeate stream. The pre-filtration unit 52 is generally designed to remove contaminants having a nominal diameter of 5 microns or greater. Consequently, the pre-filtration unit 52 can include one or more filters having a screen size ranging from about 400 to 650 count mesh. Suitable filters for use in the pre-filtration unit 52 include any conventional filter known in the art capable of withstanding alkaline conditions such as associated with the hemicaustic stream. Non-limiting examples of suitable pre-filters include bag filters, ribbon filters and self-cleaning filters. The pre-filtration unit 52 is generally positioned prior to the nanofiltration unit 50. However, as shown in FIG. 6, a buffer tank 56 may be positioned between the pre-filtration unit 52 and the nanofiltration unit 50.

The permeate stream exiting the one or more nanofiltration units 50 is an alkaline solution containing from about 2 to about 20 wt % caustic and is essentially free of hemicellulose. Residual hemicellulose remaining in the permeate stream exiting the one or more nanofiltration units 50 can generally range from about 0 to about 0.5 wt %. The permeate stream exiting the one or more nanofiltration units 50 may further contain more than 80 wt % water. Use of such dilute caustic streams may not be suitable in all subsequent applications. Consequently, in beneficial embodiments, the nanofiltration system 40 further comprises an evaporation system 54 to increase the caustic concentration of the permeate stream exiting the nanofiltration system. The evaporation system 54 may include one or more evaporators 58, advantageously positioned in series. The beneficial embodiment provided in FIG. 6 illustrates an evaporation system 54 with four evaporators 52 positioned in series. The evaporators increase the caustic concentration of the permeate stream 40b exiting the nanofiltration system 40 from an initial concentration of about 1 to 20 wt % to a final concentration of about 25 to 50 wt %.

In reference to nanofiltration systems generally, the permeate stream 40b exiting the nanofiltration system 40 may advantageously be used as an alkaline solution in any suitable application. For example, the permeate stream 40b exiting the nanofiltration system 40 may be recycled back into the steeping liquor supply system 32, as indicated in FIG. 4. The permeate stream 40b exiting the nanofiltration system 40 may typically constitute up to 100% of the alkaline solution included in the steeping liquor entering the alkaline treatment system 26. In advantageous embodiments, the permeate stream 40b exiting the nanofiltration system 40 constitutes about 80 wt % of the alkaline solution included in the steeping liquor entering the alkaline treatment system 26.

The concentrated hemicellulose stream 40a exiting the nanofiltration system 40 is likewise an alkaline solution containing up to 20 wt % caustic in water. However, the concentrate stream exiting the nanofiltration system 40 further contains from about 5 to about 30 wt % hemicellulose with a xylan purity of from about 85 wt % to about 99 wt %, and advantageously greater than 90 wt % xylan. In an advantageous embodiment achievable in accordance with the invention, the concentrate stream has a low concentration, less than about 1 wt % of lignin and other impurities.

The xylan content of the concentrated hemicellulose stream 40a may be converted to xylose and xylitol according to conventional procedures. Procedures for the conversion of xylan to xylose, and from xylose to xylitol, are described in U.S. Pat. Nos. 3,980,719, 4,025,356, 4,075,406 and 5,084,104.

The xylan content of the concentrated hemicellulose stream 40a is converted to xylose by sending the contents of the stream 40a to a hydrolysis unit 100. Hydrolysis is known in the art and may be accomplished through various alternative methods.

Referring to FIG. 7, according to an advantageous embodiment, a mineral acid (preferably sulfuric acid) 60 is added to the concentrated hemicaustic solution 40a, thereby acidifying the mixture. The resultant acidified hemicaustic stream 61 is conveyed to a hydrolysis reactor. During hydrolysis, reaction temperature can range from 90° C. to 160° C., preferably from 120° C. to 140° C., for a period ranging from 10 minutes to 10 hours, preferably for 20 to 120 minutes.

Referring to FIG. 8, the acidified hemicaustic stream 61 consists of a solution of precipitated hemicellulose (2-20% wt), aqueous sodium sulfate (0.1-110% wt), and sulfuric acid (0.1-5% wt), and it is advantageously desalted 62a prior to being conveyed to the hydrolysis reactor 70. Alkali salts may be separated from acidified hemicaustic by ion exchange, microfiltration, and centrifugation. Desalting prior to acid hydrolysis improves acid hydrolysis kinetics and reduces downstream process cost.

Alkali removal of stream 61 is advantageously accomplished by ion exchange or microfiltration, where 0% to 98% sodium removal is achieved prior to acid hydrolysis. Alternatively, alkali salt may be removed from the acidified hemicellulose stream 61 by diluting the stream with water and centrifuging to produce a paste of hemicellulose and a clear stream of salt water. After desalting 62a, the hemicellulose paste may be dissolved in an acidified solution as necessary to convey the hemicellulose to the hydrolysis reactor 70.

Referring to FIG. 9, alkali salts may be removed from the acidified hemicaustic stream 61 by a de-alkalization operation 62b, consisting of a cation exchange process, prior to being conveyed to the hydrolysis reactor 70. An exemplary de-alkalization operation 62b is described in Example 3 below.

After hydrolyzing the xylan content of the hemicellulose to xylose, the hydrolyzate is purified 76 to remove organic/inorganic acids, salts, and colored by-products from the xylose. Ion exchange resins may be used to purify the xylose. The use of ion exchange resins is a common and highly practiced technology in the commodity sugars industry for demineralizing and decolorizing sugars. Ion exchange does not, however, chromatographically separate the organic components, but rather remove undesirable impurities. Ion exchange is the preferred method of xylose purification, herein.

Ion exchange is the preferred method of xylose purification, herein, where hydrolyzed hemicellulose is contacted with an anion exchange resin in an, at least one, anion exchange process, wherein the anion exchange resin has either a weakly-basic or strongly-basic ammonium hydroxide chemical functionality. The hydrolyzed hemicellulose is further contacted with a cation exchange resin in a, at least one, cation exchange process, wherein the cation exchange resin has strongly-acidic sulfonic acid chemical functionality.

Purifying the hydrolyzate containing xylose 71 with ion exchange 76 produces a purified xylose stream 77 (>90% on solids) which can be concentrated to a crude xylose syrup using a conventional evaporator or, optionally, crystallized 78 to a high purity product 80.

The high purity of the xylose streams resulting from the invented method provides a great benefit over methods of producing xylose from raw cellulose products of the past. Previous methods resulted in xylose streams having high levels of impurities, such as lignin, organics, and non-xylan hemicellulose components, that required chromatographic separation or alcohol induced precipitation. However, chromatography or precipitation is not necessary with the invented process due to the initial high purity of the raw material, the particular processing steps specified herein, and the purity of the resulting xylose product. Avoidance of the chromatography step lowers production costs substantially and avoids delay associated with the chromatography or precipitation operations.

Either of the two xylose products can be sent directly to a hydrogenation unit to produce xylitol. The xylitol may be incorporated directly into food processing operations or may be packaged for storage or shipping.

EXAMPLES

The processes of the present invention are demonstrated in the following examples. Analytical results described in the examples were obtained using the following methods. The permanganate oxidation number of fibers and hemicellulose was determined by TAPPI Standard test method T214 m-50. The lignin content of samples was estimated by multiplying the permanganate oxidation number of a given sample by 0.23 (expressed as % wt lignin of OD fiber sample). The wood sugar content of fibers and hemicellulose was determined by hydrolyzing samples according to TAPPI Standard test methods T249 cm-85 and T222 om-98. The hydrolyzed samples were analyzed for sugar compounds by HPLC chromatography using a Dionex LC20 module equipped with an ED40 electrochemical detector, and a GP40 gradient pump. A CarboPac™ MA1 column was used for resolving sugar compounds. A 0.6 mM NaOH eluent was pumped at a 0.4 mL/min flow rate to a pulsed amperometric detector.

Inorganic compounds were analyzed using a Dionex DX-120 ion chromatography unit, running a 2 ml/m eluent, comprised of 2 mM $Na_2CO_3$ and 0.75 mM $NaHCO_3$. Detection was by suppressed conductivity. Salt ions were resolved using a Dionex AS9-SC ion chromatography column.

The intrinsic viscosity (IV) of fibers was determined by dissolving samples in cupriethylenediamine (Cuene), and measuring solution viscosity with capillary viscometers.

Molecular weight distribution of hemicellulose was determined by gel permeation chromatography (GPC). The hemicellulose in hemicaustic samples was resolved using a 1.2 m×0.5 cm (length×diameter) column packed with Sephadex® G-50. Prior to packing the column, the packing material was initially swelled in excess 0.5M NaOH solution at 90° C. for approximately one hour. After packing the column, the eluent was allowed to equilibrate under a constant flow (0.5 mL/min.) for 24 hours. Following the equilibration period, calibration standards [dextran blue 2000 (MW≈2,000,000 g/mole), five sodium polystyrene sulfonate standards ($MW_{range}$ between 1,530 g/mole and 34,700 g/mole), and methyl red (MW=269.31 g/mole)] were run through the packed column. An HP 8452A diode array UV spectrophotometer, and a Shodex RI-71 refractometer were used for detection. Actual hemicaustic samples were loaded into a 0.5 mL sample loop. Eluent flow through the column was set to 0.5 mL/min.

The following examples (1-3) demonstrate the production of high purity xylose made from the alkaline extract of a prehydrolyzed kraft hardwood fiber. The examples, further, demonstrate a process by which no chromatographic separation is required to make a high purity xylose product, and the resulting xylose product is suitable as a xylitol feedstock material. Additionally, the examples demonstrate that sodium removal prior to xylan hydrolysis is advantageous, but is not required to obtain high purity xylose product.

Example 1

Cold Caustic Alkaline Extraction

A hemicaustic solution was obtained from the Rayonier Corporation chemical cellulose mill (Jesup, Ga.—USA). The hemicaustic was a hardwood hemicellulose alkaline extract from a pre-hydrolyzed kraft fiber. The fiber was partially bleached in a conventional pulp bleaching operation prior to the hemicellulose extraction stage. The hardwood chip furnish used to make the fiber was composed of roughly 40% oak, 40% gum, and 10% maple (all hardwood species from the southeastern United States).

The components of the hardwood hemicaustic are shown in TABLE I, and are expressed as the percent weight of the hemicaustic solution. The individual sugar components of the hemicellulose are expressed as a weight percent of the total sugars liberated from the hemicellulose using the test method described above. These numbers give a relative weight fraction of the anhydrous sugar units that compose the hemicellulose. Furthermore, the average degree of polymerization (DP) and the molecular weight distribution of the hemicellulose are shown at the bottom of TABLE I.

TABLE I

Properties of Alkaline Extracted Hardwood Hemicellulose From a Prehydrolyzed Kraft Pulp

| | |
|---|---|
| NaOH (wt % of hemicaustic) | 5.01 |
| Lignin (wt % of hemicaustic) | 0.025 |
| Hemicellulose (wt % of hemicaustic) | 0.98 |
| Xylose (wt % hemicellulose) | 95.9 |
| Glucose (wt % hemicellulose) | 3.0 |
| Mannose (wt % hemicellulose) | 0.9 |
| Galactose (wt % hemicellulose) | 0.2 |
| Hemicellulose DP | 33 |
| $M_n$ (Daltons) | 1,590 |
| $M_r$ (Daltons) | 4,560 |
| Polydispersity ($M_n/M_r$) | 3.6 |

Hemicaustic Nanofiltration

A pilot nanofiltration unit manufactured by Koch Membrane Systems was used to fractionate the hemicaustic into a pure caustic stream, and a concentrated hemicellulose stream. A spiral wound, alkali resistant nanofiltration membrane (KOCH model# MPS-34) with a molecular cutoff of 200 Daltons, was used in the pilot unit and is the same type used in industrial units.

Prior to nanofiltration, hemicaustic was pre-filtered with a 5 micron filter available from US Filter Co. (model #P05 [6x26]GWE) to remove fibers and fines. Following pre-filtration, the hemicaustic was fed to the nanofiltration unit at 50° C., 25 bar, at a flow rate of 4 gpm. The hemicaustic was circulated in a closed loop through the nanofiltration unit until about 90% (by volume) of the initial feed material was passed through the membrane, producing a permeate stream of purified caustic (5.01% wt NaOH). The hemicaustic that was rejected by the membrane (roughly 10% by volume of the initial feed material) contained approximately 10% by weight hemicellulose. The concentrated hemicaustic was collected in a bin, and diluted with one equivalent volume of demineralized water. The resulting hemicaustic contained 2.48% NaOH and roughly 5% weight hemicellulose.

Again, the hemicaustic was circulated through the nanofiltration unit at 50° C. until roughly 50% (by volume) of the feed material was passed through the nanofiltration membrane. The final concentrated hemicaustic contained 2.48% wt. NaOH and 12.0% wt. hemicellulose.

Acid Hydrolysis of Hardwood Hemicellulose

A sample of the concentrated hemicaustic solution (5,209 g) was diluted with demineralized water to a total weight of 7,200 g (8.68% wt hemicellulose, 1.79% wt NaOH). A portion of the mixture (6,150 g) was acidified with 221 g of 96% sulfuric acid to give a final sample weighing 6,371 g, and composed 8.38% wt hemicellulose, 4.7% wt $Na_2SO_4$, and 1.0% wt $H_2SO_4$. The acidified concentrate was quantitatively transferred to a 2-gallon vertical Parr® reactor (model #4552). The reactor temperature was ramped up from 80° C. to 150° C. over a 25 minute period. The reaction temperature was held constant at 150° C. for an additional 40 minutes. The reactor was then cooled and its contents were collected for testing. The final solution properties of the hydrolyzate were measured, and are shown in TABLE II. The xylose and sodium sulfate content are expressed as percent weight of the solution.

TABLE II

Hydrolyzed Hemicellulose Solution Properties

| | |
|---|---|
| Xylose (wt %) | 7.36 |
| Sodium sulfate (wt %) | 4.7 |
| Specific gravity (25° C.) | 1.068 |
| pH | 1.2 |
| Xylose yield (% theoretical) | 81.0 |

Xylose Purification

Residual mineral acid, sodium salt, organic acids, and color were removed from the hydrolyzate using commercially available ion exchange resins. A 24×1.5 inch glass column was packed with 500 $cm^3$ of DOWEX™ 66 ($HO^-$ form) anion exchange resin. A second 24×1.5 inch glass column was packed with 500 $cm^3$ of DOWEX™ 88 ($H^+$ form) cation exchange resin.

A 3,000 g sample of the hydrolyzed hemicellulose (221 g of xylose at 7.36% wt) was filtered through a 0.4 µm porous acetate membrane filter to remove any suspended particles and contaminants from the hydrolyzate.

Step #1) The filtered hydrolyzate sample was fed to the column containing DOWEX™ 66 resin at a rate of 100 ml/m. The column was then washed with 0.5 liter (1 bed volume) of demineralized water to rinse any remaining xylose free from the resin bed. After collecting the treated hydrolyzate sample and the rinse water, the exchange resin was regenerated with 3 liters of 1N NaOH, and then thoroughly washed with demineralized water.

Step #2) The hydrolyzate sample from step #1 was then fed to the column containing DOWEX™ 88 cation exchange resin at a rate of 50 ml/min. Following sample addition to the column, 0.5 liter of demineralized water was used to rinse residual xylose from the resin bed. After collecting the treated hydrolyzate sample and rinse water, the exchange resin was regenerated with 1.5 liters of 0.5N $H_2SO_4$, and then thoroughly washed with demineralized water.

Step #3) The hydrolyzate sample was again run through the column containing DOWEX™ 66 using the same procedure as in step #1. The final properties of the purified xylose sample are shown in TABLE III. The xylose content of the purified sample is 97.9% weight xylose based on the total dry solids content of the solution. Thus, the xylose in the hydrolyzed hemicellulose sample has been purified, and the resulting material is suitable for hydrogenation to make xylitol. Optionally, the purified xylose product can be crystallized to a food-grade xylose product using conventional crystallization technology.

TABLE III

Properties of Purified Xylose Solution

| | |
|---|---|
| Final solution weight (g) | 3.690 |
| Total dissolved solids (wt %) | 5.78 |
| Xylose (wt %) | 5.66 |
| Glucose (wt %) | 0.07 |
| Sodium Sulfate (wt %) | 0.05 |
| Appearance | colorless, clear liquid |
| pH | 8.6 |
| Specific gravity | 1.033 |

The above example demonstrates that, to some degree, sodium salts may be present during the hydrolysis of hardwood hemicellulose without having detrimental effects on the final xylose product. However, choosing not to separate residual sodium (or any alkali metal) from hemicellulose prior to hydrolysis will result in added processing costs associated with the down-stream ion exchange purification process. Example 2 demonstrates a method of reducing xylose production cost by first "de-salting" the hemicellulose prior to the hydrolysis stage, thereby eliminating some of the required ion exchange capacity in the xylose purification step.

Example 2

A 300-gallon sample of hardwood hemicaustic was obtained from Rayonier Corporation (Jesup, Ga.—USA). The hemicaustic sample was processed using a KOCH nanofiltration unit in the same fashion as described in EXAMPLE 1. Concentrated hemicaustic generated by the nanofiltration unit contained roughly 12% wt hemicellulose and 2% wt NaOH.

Demineralization (Sodium Removal)

A portion of the concentrated hemicaustic was neutralized with 96% sulfuric acid. The resulting mixture was a milky, white slurry of precipitated hemicellulose. The neutralized mixture was filtered with a 1.21 μm porous acetate membrane filter. The resultant filter cake was a white hemicellulose "paste". The filtrate, a clear light-yellow solution of sodium salt and other dissolved materials, was discarded. The hemicellulose paste was diluted in demineralized water. Properties of the diluted hemicellulose paste were measured, and are listed in TABLE IV. The total dissolved solids, sodium sulfate, and hemicellulose content are listed as the percent weight of the solution. The wood sugars content of the hemicellulose was analyzed, and is listed as the percent weight of the hemicellulose.

TABLE IV

Properties of Desalted Hemicellulose Solution

| | |
|---|---|
| Total dissolved solids (wt %) | 13.3 |
| Sodium Sulfate (wt %) | 1.3 |
| Hemicellulose (wt %) | 11.9 |
| Xylose (wt % hemicellulose) | 98.8 |

TABLE IV-continued

Properties of Desalted Hemicellulose Solution

| | |
|---|---|
| Mannose (wt % hemicellulose) | 0.6 |
| Glucose (wt % hemicellulose) | 0.5 |
| Galactose (wt % hemicellulose) | 0.06 |
| Specific gravity (25° C.) | 1.052 |

Acid Hydrolysis

A 3.257 kg sample of the neutralized hardwood hemicellulose solution was mixed with 52 g of 96% sulfuric acid, yielding a 3.309 kg aqueous solution containing 1.29% wt $Na_2SO_4$, 11.76% wt hemicellulose, and 1.5% wt $H_2SO_4$. The mixture was transferred to a 2-gallon vertical Parr™ reactor, and heated at 140° C. for 75 minutes. The reactor was cooled, and the contents of the reactor were analyzed. The solution properties of the hydrolyzed hemicellulose are shown in TABLE V.

TABLE V

Hydrolyzed Hemicellulose Solution Properties

| | |
|---|---|
| Xylose (wt %) | 10.65 |
| Xylose yield (% theoretical) | 81.0 |
| Sodium sulfate (wt %) | 1.3 |
| Sulfuric acid (wt %) | 1.5 |
| pH | 0.4 |
| Specific gravity | 1.064 |

Xylose Purification

A 2 cm diameter glass column was packed with 190 cm³ of DOWEX™-88 cation exchange resin beads ($H^+$ form). A second 2 cm diameter glass column was packed with 190 cm³ of Amberlite™ IRA-410 anion exchange resin beads ($HO^-$ form). Both columns were flushed with 2 liters of demineralized water to rinse any inorganic compounds free from the exchange resins.

A de-ashing assembly was constructed by connecting the two columns in series. The top of the cation exchange column was initially fed with untreated hydrolyzate. The product eluted from the bottom of the cation exchange column was directly fed to the top of the anion exchange column. The bottom product from the anion exchange column was collected as a purified xylose solution; demineralized and color-free.

A 208 g sample of hydrolyzed hemicellulose (from TABLE V) was filtered with a 1.2 m porous acetate membrane. The filtrate was quantitatively fed to the top of the cation exchange column at a rate of 3 mL/min. Demineralized water was then pumped to the column assembly at a rate of 5 mL/min. A photospectrometer monitored the onset of xylose elution from the anion exchange column. Upon xylose elution from the de-ashing assembly, sample was collected for roughly 90 minutes. The final solution characteristics are shown in TABLE VI. Dissolved solids, xylose and sodium sulfate are expressed as the percent weight (dry basis) of the solution.

TABLE VI

Properties of Purified Xylose Solution

| | |
|---|---|
| Total weight (g) | 438 |
| Appearance | Clear, colorless liquid |
| Dissolved solids (wt %) | 3.39 |
| Xylose (wt %) | 3.36 |
| Sodium sulfate (wt %) | 0.03 |

The xylose product in TABLE VI can be concentrated into syrup using conventional evaporators. Also, crystallization of the xylose product can be performed using traditional methods of making sugar crystals.

In the "Demineralization" step of the present example, filtration of the precipitated hemicellulose partially removes sodium (as sodium sulfate) prior to hydrolysis. This becomes obvious when comparing TABLE II with TABLE V. In TABLE II, residual caustic soda left in the concentrated hemicaustic results in a 1.6 weight ratio of xylose to sodium sulfate. In contrast, the resulting hydrolyzed hemicellulose solution in the present example contains an 8.2 weight ratio of xylose to sodium sulfate, as shown in TABLE V. By partly removing sodium prior to hydrolysis, ion loading to subsequent ion exchange treatments is reduced, lowering the overall cost of xylose processing. Therefore, EXAMPLE 2 demonstrates an alternative lower cost method for producing high purity xylose, by which no chromatographic separation is required.

Example 3

Example 3 demonstrates yet another low cost method of producing a high purity xylose product. The same concentrated hemicaustic solution used in Example I (produced by nanofiltration of hardwood hemicaustic) is used in the following example. The concentrated hemicaustic contained 2.48% wt. NaOH and 12.0% wt. hemicellulose.

Demineralization (Sodium Removal)

A 1.25 inch diameter glass column was packed with 382 cm$^3$ of Lewatit™ CNP 80 WS cation exchange resin (H$^+$ form—manufactured by Bayer Chemical Corporation); a weakly acidic cation exchange resin made of cross-linked polyacrylic acid. A peristaltic pump was connected to the outlet of the column, and was used to draw feed material through the column, and discharge treated material into a collection bottle.

A 1.0 L sample of concentrated hemicaustic was diluted with 1.0 L of demineralized water. The mixture was heated to 50° C. in an isothermal water bath. The resin bed was then preheated to approximately 50° C. by passing 2 liters of 50° C. demineralized water through the column. Next, the 2 liters of diluted hemicaustic was delivered to the column at a rate of 200 ml/min. The hemicaustic solution was pulled through the resin bed using the peristaltic pump. Residual hemicellulose was washed from the column with a 500 ml aliquot of demineralized water. The de-alkalized hemicaustic, plus the rinse water, was collected in a plastic jug. A second batch of de-alkalized hemicaustic solution was prepared in the same manner. The resulting two solutions were combined. The final mixture had a pH of 3.0 and a specific gravity of 1.020 (at 25° C.). The total solids content was measured to be 6.67% weight, and the theoretical xylose yield was measured to be 60.2 mg xylose per gram of solution.

Acid Hydrolysis

A 3,104 g sample of de-alkalized hemicaustic solution was transferred to a 2-gallon vertical Parr® reactor (model #4552). A 8.08 g sample of 96% sulfuric acid was added to reactor contents. An additional 20 g of demineralized rinse water was added to the contents of the reactor, giving a final aqueous hemicellulose solution weighing 3,132 g, and containing 0.25% wt H$_2$SO$_4$.

The contents of the reactor were heated from 80° C. to 130° C. over a 20 minute period. The reaction temperature was held constant at 130° C. for an additional 40 minutes. The reactor was then cooled, and the contents were analyzed. The final solution properties of the hydrolyzed hemicellulose solution are shown in TABLE VII

TABLE VII

| Hydrolyzed Hemicellulose Solution Properties | |
|---|---|
| Xylose (wt %) | 5.04 |
| Sulfuric Acid (wt %) | 0.25 |
| Specific gravity (25° C.) | 1.020 |
| pH | 1.7 |
| Xylose yield (% theoretical) | 83.8 |

Xylose Purification

Residual mineral acid, organic acids, and color were removed from the hydrolysate using commercially available ion exchange resins. A 2×24 inch glass column was packed with 500 cm$^3$ of DOWEX™ 66 (HO$^-$ form) anion exchange resin. A second 2×24 inch glass column was packed with 500 cm$^3$ liter of DOWEX™ 88 (H$^+$ form) cation exchange resin.

A 2,720 g sample of the hydrolyzed hemicellulose solution (127 g xylose at 5.04% wt) was filtered through a 0.4 μm porous acetate membrane filter.

Step #1) The filtered hydrolyzate sample was quantitatively fed to the column containing DOWEX™ 66 resin at a rate of 50 ml/m. The column was then washed with 500 ml (1 bed volume) of demineralized water to rinse any remaining xylose free from the resin bed. After collecting the treated hydrolyzate sample and the rinse water, the exchange resin was regenerated with 1.5 liters of 1N NaOH, and then thoroughly washed with demineralized water.

Step #2) The partially treated hydrolyzate sample collected in step #1 was fed to the column containing DOWEX™ 88 cation exchange resin at a feed rate of 50 ml/m. Following sample addition to the column, 0.5 liter of demineralized water was used to rinse residual xylose from the resin bed. After collecting the treated hydrolyzate sample and rinse water, the exchange resin was regenerated with 1.5 liters of 0.5N H$_2$SO$_4$, and then thoroughly washed with demineralized water. At this level of purification, the sample was a clear liquid with a very light-brown tint, and had a pH of 2.7. The solution pH, compared to the original hydrolyzate sample (pH=1.7), indicates that roughly 90% of the acids originally present in the untreated hydrolyzate sample had been removed.

Step #3) The hydrolyzate sample was again run through the column containing DOWEX™ 66 using the same procedure as in step #1. The final solution had a pH of 7.3 and was a clear, colorless liquid. A portion of the final material was concentrated to a syrup using a Buchi™ rotary evaporator (model # R-200), and was subsequently analyzed for chemical content. Analytical results of the xylose syrup are shown in TABLE VIII. The analytical results showed that nearly 95% of the total dissolved solids consisted of xylose.

TABLE VIII

| Xylose Syrup Properties | |
|---|---|
| Total Dissolved Solids (wt %) | 32.9% |
| Xylose (wt % DS) | 94.8% |
| Xylobiose (wt % DS) | 1.2% |
| Glucose (wt % DS) | 2.7% |
| Mannose (wt % DS) | 0.9% |
| Sodium Sulfate (wt % DS) | 0.2% |

Crystallization

Using a using a laboratory rotary evaporator, the remaining sample of purified xylose from the Xylose Purification step was evaporated down to 170 grams of concentrated xylose syrup at roughly 80% wt xylose. The concentrated xylose syrup was then cooled in an ice bath for 2 hours, during which time xylose crystals began to form creating a slurry. The xylose crystal slurry was then placed in a refrigerator at 4° C. for 10 hours, during which time extensive crystallization occurred. The flask, containing xylose crystals and mother liquor, was then warmed to about 35° C. to increase solution viscosity. The solution was then filtered using a fritted glass filter funnel and vacuum flask. The xylose crystal filter cake was washed with 20 ml of a cold saturated aqueous solution of xylose. The resulting crystals were granulated using a rotary evaporator, and then ground into a powder using a mortar and pestle. The dry xylose powder weighed 77 g, and the xylose purity was greater than 99%. Composition of the xylose powder is shown in TABLE IX, and is expressed as weight percent on a moisture-free basis. The xylose powder can optionally be hydrogenated to xylitol, or used directly in food-grade applications.

TABLE IX

| Xylose Powder Properties | |
| --- | --- |
| Xylose (wt %) | 99.6% |
| Xylobiose (wt %) | 0.3% |
| Sodium Sulfate (wt %) | 0.05% |
| Mannose (wt %) | trace |
| Glucose (wt %) | trace |

Example 4

As mentioned above, pre-hydrolysis of the undigested wood acts to partially decompose the hemicellulose components within the wood and to lower the molecular weight of those components. The favorable result of pre-hydrolysis is that the pre-hydrolyzed hemicellulose is more easily removed from the wood during traditional cooking stages, and during subsequent cold caustic treatments, facilitating the production of high purity chemical-grade cellulose. Though the pre-hydrolysis step is necessary for producing chemical-grade pulps using the kraft process, it is not required to practice the invented method, as will be demonstrated in the following example.

A mixture of hardwood chips composed of roughly 40% oak, 40% gum, and 10% maple (all hardwood species from southeastern United States), were cooked in a conventional kraft process in a pilot-scale digester. Cooking liquor containing sodium sulfide and sodium hydroxide was added to pilot scale digester containing the hardwood chips. The kraft cooking conditions are shown in TABLE X.

TABLE X

| Kraft Cooking Conditions | |
| --- | --- |
| Liquor to wood ratio (wt/wt) | 4.2 |
| Effective alkali (EA) to wood ratio (wt/wt) | 0.140 |
| Active alkali (AA) to wood ratio (wt/wt) | 0.164 |
| Sulfidity (%) | 29.3% |
| Initial temperature | 35° C. |
| Maximum temperature | 170° C. |
| Time to maximum temperature | 85 minutes |
| Time at maximum temperature | 60 minutes |
| Total cooking time | 145 minutes |
| Total H-factor | 1106 |

A complete review of kraft cooking terminology, calculations, and theory are presented in PULP AND PAPER MANUFACTURING VOL. 5: ALKALINE PULPING, 3$^{rd}$ ed., 1989, Tappi press, Atlanta, Ga. Effective alkali (EA) is the weight of sodium hydroxide (NaOH) plus one-half the weight of sodium sulfide ($Na_2S$) that is charged to the digester, and is expressed as the equivalent weight of sodium oxide ($Na_2O$) per oven-dried weight of wood. Additionally, active alkali (AA) is the weight of NaOH plus the total weight of $Na_2S$, expressed as the equivalent weight of $Na_2O$ on a dry wood basis. The sulfidity of the cooking liquor is expressed as a weight percentage by the following equation:

$$\text{Sulfidity}(\%) = [½(Na_2S)/(NaOH + ½Na_2S)] \times 100$$

Last, H-factor is a unitless measurement used to predict the extent of delignification of wood chips. H-factor calculations are based on chemical reaction kinetic theory and empirical data.

The pulp produced from the kraft cook was washed with demineralized water, and screen in a flat screen to remove knots and shives. The final screened brown stock pulp properties are shown in TABLE XI. All yield data is expressed on an oven dried basis (OD).

TABLE XI

| Properties of Brown Stock Kraft Hardwood Fibers | |
| --- | --- |
| Screened pulp yield (% OD wood) | 46.9 |
| Brown stock permanganate number | 10.6 |
| Acid insoluble lignin (wt % on OD Fiber) | 2.4% |

Bleaching

The hardwood kraft brown stock pulp was bleached in a conventional pulp bleaching process using a $DE_p$ bleaching sequence. The bleaching conditions for each stage are shown in TABLE XII. All chemical charges are expressed as percent weight on OD fiber.

TABLE XII

| Bleaching Stage | Chlorine Dioxide (D) | Hot Alkaline Extraction ($E_p$) |
| --- | --- | --- |
| Time (minutes) | 25 | 45 |
| Temperature (C.) | 50 | 80 |
| Pulp consistency (%) | 3.5 | 10 |
| Chlorine Dioxide (%) | 1.2 | — |
| Hydrogen peroxide (%) | — | 1.0 |
| Magnesium sulfate (%) | — | 0.1 |
| Sulfuric Acid (%) | 0.5 | — |
| Sodium Hydroxide (%) | — | 3.0 |
| Starting pH | 2.4 | — |
| End pH | 2.0 | 12.1 |

Following the Ep-stage, fiber properties of the "semi-bleached" non-prehydrolyzed hardwood kraft fiber were measure. Test results are shown in TABLE XIII. Based on the permanganate number of the semi-bleached fiber, greater than 80% of the residual fiber lignin was removed during the bleaching process. Fiber samples were also hydrolyzed and tested for sugar content. Based on the wood sugar analysis of the semi-bleached fibers, roughly 20% of the fiber composition is made of hemicellulose, denoted by the sum of the xylose and mannose sugar components, which are associated with xylan and mannan components of hemicellulose.

TABLE XIII

Properties of Semi-bleached Kraft Hardwood Fibers (Post-Ep Stage)

| | |
|---|---|
| ISO Brightness (%) | 80 |
| Permanganate number | 2.1 |
| Xylose (wt % of fiber) | 19.3 |
| Mannose (wt % of fiber) | 0.5 |
| Σ{xylose + mannose} (wt % of fiber) | 19.8 |
| Cuene IV (dL/g) | 7.4 |

Cold Caustic Alkaline Extraction

Hemicellulose was extracted from the semi-bleached kraft pulp in an aqueous slurry of sodium hydroxide. The conditions used to extract hemicellulose from the pulp are shown in TABLE XIV. Following pulp extraction, hemicaustic liquor was collected

TABLE XLV

Cold Caustic Alkaline Extraction Conditions

| | |
|---|---|
| Time (minutes) | 15 |
| Temperature (C.) | 45 |
| Pulp consistency (%) | 4.0 |
| NaOH (% wt. in solution) | 6% | by filtering the wood fibers out of the extraction liquor using a wire screen mesh. Hemicellulose was isolated from the hemicaustic liquor by first neutralizing the liquor with sulfuric acid, and then centrifuging the precipitated hemicellulose from the neutralized liquor. Analysis of the precipitated hemicellulose shows that it is composed predominately of xylan (see TABLE XV). It follows, then, that treatment of the extracted hemicellulose in the manner indicated in EMAPLES I, II, and III should produce a high purity xylose syrup (or crystal) that can be used in direct applications for food, or for the manufacturing of xylitol.

TABLE XV

Wood Sugar Composition of Extracted Hardwood Hemicellulose From Kraft Pulp

| | |
|---|---|
| Xylose (%) | 99.3 |
| Glucose (%) | 0.7 |
| Mannose (%) | trace |
| Galactose (%) | trace |

Example 4 demonstrates the production of a high purity xylan made from the alkaline extract of a partially bleached paper-grade hardwood fiber. The example demonstrates another potential source of high purity xylan, other than hemicellulose extract from a pre-hydrolyzed hardwood kraft fiber, which could be processed into high purity xylose using the present invention outlined in EXAMPLES 1, 2, and 3. As demonstrated in EXAMPLES 1 through 3, no chromatographic separations or costly alcohol precipitation steps are required to make a high purity xylose product.

Having the benefit of the teachings presented in the foregoing descriptions and the associated drawings, many modifications and other embodiments of the inventions set forth herein will come to mind to one skilled in the art to which these inventions pertain. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of producing xylose from a cellulose material containing hemicellulose, comprising:
   providing a pre-hydrolyzed cellulose pulp that is at least partially bleached and has a hemicellulose content that is predominantly xylan, and a lignin content that is less than 1 wt. %;
   extracting the hemicellulose from the at least partially bleached pulp into a caustic solution thereby forming a hemicaustic solution;
   separating the hemicaustic solution into a concentrated hemicellulose solution and a concentrated caustic solution; and,
   hydrolyzing the hemicellulose from the concentrated hemicellulose solution to produce xylose.

2. The method of claim 1, wherein the step of providing pulp comprises providing hardwood pulp wherein the pulp is greater than 4 wt % hemicellulose.

3. The method of claim 1, wherein the step of providing pulp comprises providing hardwood pulp where the hemicellulose is greater than 85 wt % xylan.

4. The method of claim 1, wherein the step of providing the at least partially bleached the pulp comprises providing a cooked cellulose pulp and subjecting the cooked pulp to a series of oxidation and extraction stages until greater than 80 wt % of the original lignin content of the pulp has been removed.

5. The method of claim 1, wherein the step of proving the at least partially bleached pulp comprises providing a cooked cellulose pulp and subjecting the cooked pulp to a series of oxidation and extraction stages until the pulp has an ISO brightness of 88% or higher.

6. The method of claim 1, wherein the step of extracting the hemicellulose from the pulp comprises extracting the hemicellulose using a cold caustic treatment.

7. The method of claim 6, wherein the pulp has a consistency of about 2 wt % to about 50 wt % with respect to the caustic solution during cold caustic treatment.

8. The method of claim 7, wherein the caustic solution has a pH greater than 13 during treatment.

9. The method of claim 8, wherein a temperature of the caustic solution is from about 20° C. to about 50° C. during treatment.

10. The method of claim 6, wherein the cold caustic treatment is continued until the treated pulp contains no more than 15 wt % hemicellulose.

11. The method of claim 10, wherein the cold caustic treatment is continued until the treated pulp contains no more than 5 wt % hemicellulose.

12. The method of claim 6, wherein a temperature of the caustic solution is less than 50° C. during treatment.

13. The method of claim 1, wherein the step of extracting the hemicellulose from the pulp into a caustic solution comprises holding the pulp in the caustic solution for a period of time and thereafter washing the pulp with water, wherein the caustic solution, extracted hemicellulose, and wash water form the hemicaustic solution.

14. The method of claim 1, wherein the step of separating the hemicaustic solution into a concentrated hemicellulose solution and a concentrated caustic solution comprises subjecting the hemicaustic solution to a separation technique selected from the group consisting of nanofiltration, distillation, centrifugation, and precipitation.

15. The method of claim 14, wherein the step of separating the hemicaustic solution comprises filtering the solution through a nanofiltration apparatus wherein the permeate stream exiting the nanofiltration apparatus is the concentrated caustic solution having greater than about 80 wt % of the original caustic solution, and wherein the concentrate stream is the concentrated hemicellulose solution that constitutes from about 5 wt % to about 30 wt % hemicellulose.

16. The method of claim 1, wherein the step of hydrolyzing the hemicellulose from the concentrated hemicellulose solution comprises acidifying the concentrated hemicellulose solution with a mineral acid; and, acid hydrolyzing the hemicellulose, whereby the xylan content of the hemicellulose is converted to xylose.

17. The method of claim 16, further comprising the step of demineralizing the acidified concentrated hemicellulose solution prior to the acid hydrolyzing step.

18. The method of claim 17, wherein the step of demineralizing is accomplished by filtration.

19. The method of claim 16, further comprising the step of demineralizing the concentrated hemicellulose solution prior to the acidifying step.

20. The method of claim 19, wherein the step of demineralizing is accomplished by ion exchange.

21. The method of claim 16, further comprising the step of removing organic/inorganic acids, metal salts, and colored by-products from the hydrolyzed hemicellulose.

22. The method of claim 21, wherein the step of removing acids, salts, and by-products from the hydrolyzed hemicellulose comprises contacting the hydrolyzed hemicellulose with a cationic ion exchange resin.

23. The method of claim 21, wherein the step of removing acids, salts, and by-products from the hydrolyzed hemicellulose comprises contacting the hydrolyzed hemicellulose with an anionic ion exchange resin.

24. The method of claim 1, wherein the resulting hydrolyzed hemicellulose has a xylose content of greater than 90 wt %.

25. The method of claim 1, wherein the step of providing a pulp comprises providing a hardwood selected from sweet gum, black gum, maple, oak, eucalyptus, poplar, beech, aspen, and mixtures thereof;

digesting the hardwood to a hardwood pulp; and, at least partially bleaching the digested pulp.

26. The method of claim 1, wherein the step of providing a pulp comprises pre-hydrolyzing a hardwood feed material;

digesting the pre-hydrolyzed hardwood; and, at least partially bleaching the digested pulp using a conventional pulp bleaching process.

27. A process for producing a xylose product from a cellulose material, comprising the steps of:

at least partially chemically bleaching a cooked pre-hydrolized cellulose pulp using a conventional pulp bleaching process to provide a pre-hydrolyzed cellulose pulp that is at least partially bleached and has a hemicellulose content that is predominantly xylan, and a lignin content that is less than 1 wt. %;

using a cold caustic treatment to extract hemicellulose from the at least partially bleached cellulose pulp into a caustic solution thereby forming a hemicaustic solution;

separating the hemicaustic solution by nanofiltration into a concentrated hemicellulose solution and a concentrated caustic solution; and, hydrolyzing the hemicellulose from the concentrated hemicellulose solution.

28. The process of claim 27, wherein the step of providing a cellulose pulp comprises providing a hardwood pulp wherein the hardwood is greater than 5 wt % hemicellulose.

29. The process of claim 28, wherein the hemicellulose of the hardwood is greater than 85 wt % xylan.

30. The process of claim 27, wherein the at least partially bleached pulp has an ISO brightness of 88% or higher.

31. The process of claim 27, wherein the cold caustic treatment is continued until the treated pulp contains no more than 15 wt % hemicellulose.

32. The process of claim 31, wherein the cold caustic treatment is continued until the treated pulp contains no more than 5 wt % hemicellulose.

33. The process of claim 27, wherein the step of nanofiltering the hemicaustic solution comprises filtering the solution through a nanofiltration apparatus wherein the permeate stream exiting the nanofiltration apparatus is the concentrated caustic solution having greater than about 80 wt % of the original caustic solution, and wherein the concentrate stream is the concentrated hemicellulose solution that constitutes from about 5 wt % to about 30 wt % hemicellulose.

34. The process of claim 27, wherein the step of hydrolyzing the hemicellulose from the concentrated hemicellulose solution comprises neutralizing the concentrated hemicellulose solution with a mineral acid; and, acid hydrolyzing the hemicellulose, whereby the xylan content of the hemicellulose is converted to xylose.

35. The method of claim 34, further comprising the step of demineralizing the concentrated hemicellulose solution prior to the acid hydrolyzing step.

36. The process of claim 34, further comprising the step of removing organic/inorganic acids, metal salts, and colored by-products from the hydrolyzed hemicellulose.

37. The method of claim 27, further comprising the step of acidifying the concentrated hemicellulose solution prior to the hydrolyzing step.

38. The process of claim 27, wherein the resulting hydrolyzed hemicellulose has a xylose content of greater than 90 wt %.

39. A method of producing xylose from a cellulose material containing hemicellulose, comprising:

providing a cellulose pulp that is at least partially bleached and has a hemicellulose content that is predominantly xylan, and a lignin content that is less than 1 wt. %;

extracting the hemicellulose from the at least partially bleached pulp into a caustic solution thereby forming a hemicaustic solution;

separating the hemicaustic solution into a concentrated hemicellulose solution and a concentrated caustic solution; and, hydrolyzing the hemicellulose from the concentrated hemicellulose solution to produce a xylose product having a purity of 80 wt % or greater in the absence of an additional purification step.

* * * * *